United States Patent [19]

Landy

[11] Patent Number: 4,976,970

[45] Date of Patent: Dec. 11, 1990

[54] PHARMACEUTICAL COMPOSITION AND METHOD FOR TREATMENT OF DIGESTIVE DISORDERS

[76] Inventor: Wady N. Landy, Taine No. 223, Polanco Mexico, D.F., 11570, Mexico

[21] Appl. No.: 315,339

[22] Filed: Feb. 24, 1989

[51] Int. Cl.$^5$ ...................... A61K 33/04; A61K 35/78
[52] U.S. Cl. .................................... 424/705; 424/713; 424/714; 424/196.1
[58] Field of Search ............. 424/705, 713, 714, 196.1

[56] References Cited

U.S. PATENT DOCUMENTS 4,216,207  8/1980  Puscas et al. ....................... 424/713

FOREIGN PATENT DOCUMENTS 453956  9/1936  United Kingdom ................ 424/714

Primary Examiner—Frederick E. Waddell
Attorney, Agent, or Firm—Ladas & Parry

[57] ABSTRACT

This invention relates to a new pharmaceutical composition and method for treatment of digestive disorders.

11 Claims, No Drawings

PHARMACEUTICAL COMPOSITION AND METHOD FOR TREATMENT OF DIGESTIVE DISORDERS

Herein is described a pharmaceutical composition which provides an inhibitory action of the gastric secretion thus making it useful for the treatment of digestive disorders. The composition comprises clofibrate, sulphur sublimate or flower of sulphur and tar as active ingredients.

BACKGROUND OF THE INVENTION

So far the most used medicines in the treatment of gastric disorder have been anticholinergic drugs which inhibit pain; antihistaminics which block receptors $H_2$ preventing the release of hydrochloric acid, aluminium and magnesium gels which neutralize hydrochloric acid in the stomach, and in some cases tranquilizers to control nervous stress.

Peptic ulcers are circumscribed to the mucous membrane which lies across the muscular membrane of the mucous, specially in areas drained by acids and pepsins, and even more frequently in the first centimeter of the doudenum being thus duodenal ulcers the cost frequent.

Apparently peptic ulcers develop due to an excessive acid or pepsin secretion thus breaking down the equilibrium between the acid and pepsin secretion with the other factors which protect the mucous such as the mucus production or the membranes which act as barrier against the permeability of the mucous cells.

The treatment of said peptic ulcers is directed towards neutralizing or reducing the gastric acidity and at present known treatments are such as suitable diet or the use of medicines like antiacids whose cure capacity or prevention of symptomatology recurrence has not been proven; and anticholinergic drugs which delay the emptying of the stomach and thus prolong retention of the antiacid and the reduction of acid secretion; however it has been shown that the results are not constant and is necessary at times to increase the dose or wake the patient up during the night to administer an extra-dose, which in addition may have negative effect such as a possible pyloric obstruction; carbenzolone is another medication used with little success specially in the treatment of duodenal ulcers; ramitivine inhibits gastric secretion on the same level as histaminic receptors and cymetidine which acts as a $H_2$ receptor for the acid and pepsin producing cells in the stomach.

SUMMARY OF THE INVENTION

The present invention is based on a new medicament with a specifically curative action in numerous gastric as well as duodenal processes thus controlling illnesses such as colitis, constipation, esophagitis, gastritis, indigestion, acidity, peptic ulcer, and duodenal ulcers, as well as to eliminate the nausea and vomiting which are indispositions typical of pregnancy.

According to the invention it is provided a pharmaceutical composition comprising: clofibrate, sulphur sublimate or flower of sulphur and tar as active ingredients.

DETAILED DESCRIPTION OF THE INVENTION

The new pharmaceutical composition has an inhibitory action of the hydrocloric acid secretions, regulates the performance of the gastric as well as intestinal mucouses, normalizing their secretions correcting the pH, and hastening the healing of the ulcers; and which comprises:
- 37.5% by weight of sulphur sublimate or flower of sulphur
- 50% by weight of tar; and
- 12.5% by weight of clofibrate, wherein said percentages are based on the total weight of the composition.

The composition of the present invention may be prepared as follows:

At room temperature and pressure, the clofibrate is added slowly to the sulphur sublimate previously ground into a powder, stirring the mixture moderately until an homogeneous mixture is obtained. Once the sulphur is saturated with the clofibrate, the tar which has previously been ground is added slowly until a sticky paste has been obtained.

However as a result of numerous tests carried out, the inventor has found that the order in which these compounds are added does not matter since the efficiency of the composition obtained is finally the same.

The sulphur used in the present invention is keratolitic and is partially converted into a sulphide providing a cathartic effect. The absorbed sulphide is eliminated as sulphate.

The metabolism of sulphur is notably parallel to that of nitrogen, the liver eliminates it as sulphuric acid and urea, the endogenous metabolism of sulphur in some way produces neutral sulphur but the mechanism is unknown.

Tar known as "Tar Oil" and "Rectified Tar Oil" is a distilled and volatile oil obtained from wood; its main constituents are phenolic substances and some hydrocarbons. Its appearance is that of an oily liquid with little color when fresh and which is rapidly degraded acquiring a reddish brown color with a density between 0.86 and 0.9.

Up to now the known therapeutic uses of tar are as an antiseptic for external application, dermatologic, and has been used as an expectorant.

The tar used in the present invention presents the following analysis:

| Determination | Analysis of Tar Result | Method |
| --- | --- | --- |
| Identification | Positive Dimerized Resinic Acids | Graphic 7 Spectroscopy of IR |
| N° of Saponification mg/KOH g sample | 9.0 | ASTM-D-464 |
| N° of Acid mg KOH/g sample | 131.0 | ASTM D 465 |
| Ashes % to 55° C. | 0.03 | ASTM D 1063 |
| Non Saponifiable % | 3.30 | ASTM D 1065 |
| Melting Point °C. | 90–94 | Fisher |
| Resinic Acids % | | Standardization by Chromatography of Gases |
| Pimaric | 12.41 | |
| Palustric | 10.56 | |
| Isopimaric | 20.86 | |
| Abietic | 14.02 | |
| Dihydroabietic | 31.60 | |
| Others | 10.50 | |

Clofibrate is a product which is found in an oleaginous condition and a boiling point of from 148° to 150° C. The chemical names of this product are 2-(4-chlorophenoxy)-2-methylpropanoic acid ethyl ester; ethyl 2-(para-chlorophenoxy)-2-methyl propionate; and ethyl para-chlorophenoxy isobutirate of the formula:

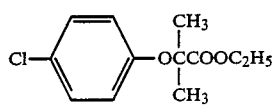

Up to now the known therapeutic use of the clofibrate is as antihyperlipoproteinemic and for reducing the concentration of cholesterol in the blood.

This pharmaceutical composition may be formulated so as to be suitable for oral administration. For such purposes the active ingredients can be mixed with suitable known excipients and incorporated by known means into such formulations such as tablets, capsules, suspensions, emulsions, solutions or dispersable powders.

PHARMACOLOGY

The new medicament acts directly on the gastric juice secretion normalizing its flow and inhibiting its excessive secretion. This modification is maintained even after the treatment has been discontinued after the last ulcer has healed. It acts on the mucous hastening the healing process and achieving its histological integrity rapidly.

DOSE

The dosage administered to the patients undergoing treatments which were successfully carried out has been 300 mg repeating said dose 2 or 3 times a day before or after meals. Likewise the laboratory experiments with dogs have verified that even though the dose is very strong, the product is not toxic in any aspect.

TESTS CARRIED OUT IN THE LABORATORY

The new medicament was used in two sample lots of animals with different preparation in order to find out the anti-secreting activity of the gastric juice.

The first group consisted of three mongrel dogs whose weight was between 28.5 to 36.8 pounds (14 to 18 kgs). Surgery for a Pavlov stomach was practiced on each one. Once they had fully recovered from surgery, they were trained in the laboratory and the following experiment was initiated: the animal was fed with balanced commercial products. The stimulus was the food and once a satisfactory plateau was obtained, each one was given three capsules of the substance studied every other day. At the same time control studies were alternated with the above dosage in order to find out the secretion capacity of each animal.

On the other sample group of eight dogs who were also mongrels surgery for a Hei-denhain stomach was practiced—transplanting the anthrogastric to the colon reestablishing—the flow in the digestive channel be means of a gastroduodenal anastomosis. Once the animals were fully recovered from—surgery the secretion from the Heidenhain stomach was quantified daily. Four of the animals were used as the control group while the others were given a capsule of the drug studied during one month. The animals were sacrificed a month after they began taking the drug.

The results were as follows:

70 experiments with the drug were carried out on the three dogs with the Pavlov stomach and 51 control experiments. The secretion in the control experiments remained constant during 4 or more hours, only a mild tendency towards a lower secretion being observed from the second hour.

On the administering the drug in the study an important decrease in the gastric secretion of the Pavlov stomach was shown which became apparent from the moment the drug was taken and—which had a different magnitude in each animal. As an average the inhibition percentage was 80. The inhibition referred to above was observed to last up to three hours in dogs U-1 and U-3 and in dog U-2 although the inhibition existed, gastric—secretion leaks were observed to occur in isolation and—approximately every hour; these leaks were never similar to the secretion values observed before administering the drug.

In respect to the anthrogastric transplant to the colon it was observed that in the control group, three of the animals—developed a peptic ulcer in the gastroduodenal anastomosis—evidently on the duodenal side; all of the animals experimented changes in gastritis verified by microscopy. Of the other four animals participating in the experiment who received the capsule, studied during one month, two showed ulceration in the same place as those in the former group and also experimented changes in gastritis. The autopsy of the other two animals showed they had normal stomach.

As was previously mentioned all the former animals were sacrificed one month after they began taking the substance being studied and no endocrine injury was found.

Because of the results obtained, we believe that this drug is able to inhibit gastric secretion in a percentage close to 80%. The inhibition obtained is maintained during three or four hours. It is possible that this effect will last even for a longer time but this is not known since this aspect was not studied.

In respect to the hipersecretion and ulcerogenic capacity of the transplant of the stomach to the colon, the ulceration frequency in the control and experimental groups was observed to be different. Seventy five percent of the animals in the control group developed peptic ulceration and all the animals had gastritis changes which was all ratified by microscopy. On the other hand only two of the four animals who received the drug experimented peptic ulceration that is 50%, besides, these animals showed usual changes in gastritis. The other two animals in the group showed completely normal stomachs which was verified by microscopy in the autopsy.

The dosage administered in both groups did not exhibit intoxication symptoms.

In the light of the above experiments, it was concluded that this composition has a similar effect to that of the propantheline or quaternary ammonium derivatives in which regards to the gastric secretion of hormonal origin.

VERIFICATION OF CLINICAL TESTS

The activity of the present composition is hereby shown by means of careful studies of 200 cases of ulcers confirmed by X-rays, laboratory analysis and other clinical techniques, so that a result of 95% effective cures was obtained. All of the cases in which cures were effective have been confirmed by analysis and X-rays. The studies were made on patients whose illnesses presented varying degrees of seriousness and chronicity;

however, when the medication was administered all of them presented a slight improvement in a short time (approximately 15 days). The treatment has had a duration of one month approximately, a record time for the complete healing and disappearance of the symptoms in all the patients.

The patients who voluntarily submitted to the treatment were not given strict diets but were told not to ingest greasy food or food which produced irritation.

This composition has also been given to pregnant women who had indispositions which cause nausea or vomiting and in the majority of cases these indispositions disappeared while, at the same time, it has been proven that the health of the foetus is not affected.

I claim:

1. A pharmaceutical composition for the treatment of digestive disorders which comprises: 37.5% by weight of sulphur sublimate or flower of sulphur; 50% by weight of tar and 12.5% by weight of clofibrate, wherein said percentages are based on the total weight of said composition.

2. A pharmaceutical composition according to claim 1, for oral use in the treatment of patients suffering from peptic ulcers, duodenal ulcers, gastritis, colitis and acidity.

3. A pharmaceutical composition according to claim 1, for oral administration to patients suffering from nausea and vomiting during pregnancy.

4. A method for the treatment of peptic ulcers, duodenal ulcers, gastritis, colitis and acidity in a patient which comprises the oral administration thereto of an effective dose of the composition of claim 1.

5. A method according to claim 4, wherein the effective dose of the composition of claim 1 is from 600 to 900 mg daily.

6. A method according to claim 4, wherein the composition is administered in tablet form.

7. A method according to claim 4, wherein the composition is administered in capsule form.

8. A method according to claim 4, wherein the composition is administered in suspension form.

9. A method according to claim 4, wherein the composition is administered in emulsion form.

10. A method according to claim 4, wherein the composition is administered in solution form.

11. A method according to claim 4, wherein the composition is administered for 15 to 30 days.

* * * * *

UNITED STATES PATENT AND TRADEMARK OFFICE
CERTIFICATE OF CORRECTION

PATENT NO. : 4,976,970

DATED : December 11, 1990

INVENTOR(S) : Wady Nader Landy

It is certified that error appears in the above-identified patent and that said Letters Patent is hereby corrected as shown below:

ON TITLE PAGE:

change "[76] Inventor: Wady N. Landy" to -- [76] Inventor: Wady Nader Landy--

Signed and Sealed this

Twenty-eighth Day of April, 1992

Attest:

HARRY F. MANBECK, JR.

Attesting Officer

Commissioner of Patents and Trademarks